US011536123B1

(12) United States Patent
Pu et al.

(10) Patent No.: US 11,536,123 B1
(45) Date of Patent: Dec. 27, 2022

(54) METHOD FOR ENHANCING THE RECOVERY FACTOR OF HEAVY OIL BY IN-SITU OIL-WATER EMULSION WITH HIGH PHASE INVERSION POINT

(71) Applicant: Southwest Petroleum University, Chengdu (CN)

(72) Inventors: Wanfen Pu, Chengdu (CN); Lin Sun, Chengdu (CN); Jianyong Xie, Chengdu (CN); Shishi Pang, Chengdu (CN); Yan Shi, Chengdu (CN); Yanjie Chu, Chengdu (CN); Rui Liu, Chengdu (CN); Daijun Du, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 4 days.

(21) Appl. No.: 17/694,508

(22) Filed: Mar. 14, 2022

(30) Foreign Application Priority Data

Jul. 14, 2021 (CN) .................... 202110794431 .X

(51) Int. Cl.
*E21B 43/20* (2006.01)
*G01N 33/28* (2006.01)

(52) U.S. Cl.
CPC ......... *E21B 43/20* (2013.01); *G01N 33/2823* (2013.01); *Y10T 436/21* (2015.01)

(58) Field of Classification Search
CPC .. G01N 33/28; G01N 33/2823; Y10T 436/21; E21B 43/20
USPC ........................................ 436/25, 28, 29, 60
See application file for complete search history.

(56) References Cited

U.S. PATENT DOCUMENTS

| 3,500,922 | A | * | 3/1970 | Holm | .................. | C09K 8/58 |
| | | | | | | 166/270.1 |
| 4,582,138 | A | * | 4/1986 | Balzer | ................ | C09K 8/584 |
| | | | | | | 507/261 |
| 4,966,235 | A | * | 10/1990 | Gregoli | ............. | B01F 23/4105 |
| | | | | | | 166/305.1 |
| 5,855,243 | A | * | 1/1999 | Bragg | .................. | E21B 43/16 |
| | | | | | | 166/305.1 |
| 2014/0042058 | A1 | | 2/2014 | Janssen et al. | | |
| 2021/0172311 | A1 | | 6/2021 | Fathi et al. | | |

FOREIGN PATENT DOCUMENTS

| CN | 102939354 | A | | 2/2013 |
| CN | 104449629 | A | | 3/2015 |
| CN | 106644913 | A | | 5/2017 |
| CN | 110016329 | A | | 7/2019 |
| CN | 110079291 | A | | 8/2019 |
| CN | 110173244 | A | | 8/2019 |
| CN | 110776899 | A | | 2/2020 |
| CN | 112210358 | A | | 1/2021 |
| CN | 112266775 | A | | 1/2021 |
| WO | 2020/263098 | | * | 12/2020 |

OTHER PUBLICATIONS

Title of the item: Xinjiang Petroleum Geology Publication Date: Dec. 1, 2015 Name of the Author: Xie Jianyong et al. Article Title: Approach to Deep Heavy Oil Viscosity Limit by Waterflooding Process: A Case Study of Wellblock Ji-7 in Changji Oilfield, Junggar Basin.
Title of the Item: China Academic Journal Electronic Publishing House Publication Date: Mar. 25, 2017 Name of the Author: Lu Laiming Article Title: Experimental Study on In-situ Self-emulsification of Heavy Oil for Enhanced Oil Recovery pp. 1-61.
Title of the Item: Journal of Petroleum Science and Engineering Publication Date: Dec. 31, 2018 Name of the Author: Uma A et al. Article Title: A review of petroleum emulsions and recent progress on water-in-crude oil emulsions stabilized by naturalsurfactants and solids.
Title of the Item: Journal of Petroleum Science and Engineering Publication Date: Mar. 6, 2019 Name of the Author: Shishi Pang et al. Article Title: Investigation into the properties of water-in-heavy oil emulsion and itsrole in enhanced oil recovery during water flooding.
Title of the Item: Industrial & Engineering Chemistry Research Publication Date: Dec. 31, 2011 Name of the Author: Galindo-Alvarez J et al. Article Title: Viscous oil emulsification by catastrophic phaseinversion:influence of oil viscosity and process conditions pp. 5575-5583.

* cited by examiner

*Primary Examiner* — Maureen Wallenhorst

(57) ABSTRACT

The present invention discloses a method for enhancing the recovery factor of heavy oil by in-situ oil-water emulsion with high phase inversion point, and the method is aimed at the development of heavy oil reservoir by water injection under the condition that the performance parameters of crude oil emulsion meet the following three specific requirements: (A) The viscosity of the crude oil is less than 6,000 mPa·s; (B) At the reservoir temperature, the phase inversion point of the crude oil emulsion is greater than or equal to 70%, and the emulsion viscosity corresponding to the phase inversion point is 2-6 times of the crude oil viscosity; (C) At the reservoir temperature, when the water cut is less than or equal to the phase inversion point, the flow rate ratio of crude oil emulsion to crude oil is 0.2 to 0.9.

6 Claims, 2 Drawing Sheets

METHOD FOR ENHANCING THE RECOVERY FACTOR OF HEAVY OIL BY IN-SITU OIL-WATER EMULSION WITH HIGH PHASE INVERSION POINT

CROSS-REFERENCE TO RELATED APPLICATIONS

The application claims priority to Chinese patent application No. 202110794431.X, filed on Jul. 14, 2021, the entire contents of which are incorporated herein by reference.

TECHNICAL FIELD

The present invention pertains to the technical field of oil production, in particular to a new method for enhancing the recovery factor of heavy oil by in-situ oil-water emulsion with high phase inversion point.

BACKGROUND

As an important resource for world economic development, the potential reserves of heavy oil worldwide are 6 times of the proven geological reserves of conventional crude oil. The heavy oil resources account for about 30% of the total oil resources in China, and its efficient development is of great significance to guaranteeing national energy security. Compared with other heavy oil production methods, water injection and displacement requires the smallest investment and the lowest energy consumption. However, due to the evident difference in viscosity between heavy oil and water, both sweep efficiency and recovery factor are low in the water flooding of heavy oil. In general, water flooding is only applicable to ordinary heavy oil with a viscosity of less than 150 m·Pas under reservoir conditions. At present, the main technical solution to enhance the recovery factor of heavy oil by water flooding at home and abroad is to reduce the viscosity difference between the oil and water, which can be achieved by adding viscosity-enhancing substances such as polymers to increase the water viscosity while using viscosity reducer, oil-in-water emulsion, $CO_2$ and other regents to reduce the oil viscosity. However, these additional substances not only increase the cost and technical difficulty of water injection, but also bring about reservoir damage and difficult treatment of produced fluid. Therefore, it is especially important to enhance the recovery factor of heavy oil at low cost and high efficiency.

Practices in a large number of reservoirs have shown that oil-water emulsification is common in water flooding due to the existence of natural active components in crude oil. In the early stage of reservoir development, the crude oil emulsion is of water-in-oil type due to high oil saturation. According to the phase inversion rule of emulsion, its phase state will be reversed from water-in-oil type to oil-in-water type with the increase of water-to-oil ratio of emulsion. The water cut increases the fastest in the high-permeability zone which is the main water flow channel in the reservoir. If the emulsion formed by heavy oil and water is low in the phase inversion point, the emulsion in the high-permeability zone will be the first to transform into oil-in-water type under low water cut. With the progress of reservoir development, the comprehensive water cut of the reservoir increases continuously, the viscosity of oil-in-water emulsion in high-permeability zone decreases continuously, while the viscosity of water-in-oil emulsion in low-permeability zone continues to rise, leading to the intensification of viscous fingering and the reduction of front-edge displacement efficiency, which is not conducive to crude oil recovery. If the emulsion formed by heavy oil and water has a high phase inversion point, the emulsion in the high-permeability zone can be kept in water-in-oil type at a higher water cut. With the increase of water cut, the emulsion viscosity in high-permeability zone is significantly greater than that in low-permeability zone, and the front edge of oil-water displacement will be automatically stabilized. Therefore, whether the heavy oil and water can form an emulsion with high phase inversion point and controllable viscosity is the key to determining whether the heavy oil reservoir can obtain the ideal recovery factor by water injection.

SUMMARY

The purpose of the present invention is to a method for enhancing the recovery factor of heavy oil by in-situ oil-water emulsion with high phase inversion point so as to solve the problem of low recovery factor in the existing water flooding method for producing heavy oil.

The method for enhancing the recovery factor of heavy oil by in-situ oil-water emulsion with high phase inversion point disclosed by the present invention is aimed at the development of heavy oil reservoir by water injection under the condition that the performance parameters of crude oil emulsion meet the following three specific requirements (A, B and C):

(A) The viscosity of the crude oil is less than 6,000 m·Pas;
(B) At the reservoir temperature, the phase inversion point of the crude oil emulsion is greater than or equal to 70%, and the emulsion viscosity corresponding to the phase inversion point is 2-6 times of the crude oil viscosity;
(C) At the reservoir temperature, when the water cut is less than or equal to the phase inversion point, the flow rate ratio of crude oil emulsion to crude oil is 0.2 to 0.9.

The method for determining whether the heavy oil reservoir meets these three specific requirements is as follows:

Step 1: Take a crude oil sample from the heavy oil reservoir, determine the crude oil viscosity, and determine whether the crude oil viscosity meets the requirement of less than 6,000 m·Pas; if it does, proceed to Step 2.

Step 2: Measure the phase inversion point of the crude oil emulsion at the reservoir temperature, and determine whether the phase inversion point is greater than or equal to 70% and whether the emulsion viscosity corresponding to the phase inversion point is 2-6 times of the crude oil viscosity; if it does, proceed to Step 3.

The method for determining the phase inversion point of the crude oil emulsion is as follows:

(1) Preheat the crude oil and produced water of a heavy oil reservoir to the reservoir temperature respectively;
(2) Mix the preheated crude oil and produced water in different volume ratios to form a system with different water cut, and stir it with an emulsifier for 60 minutes at the reservoir temperature and shear rate of 150 $s^{-1}$ to form a crude oil emulsion;
(3) Measure the viscosity of the crude oil emulsion at 7.34 $s^{-1}$ and reservoir temperature with a rotary viscometer; work out the curve on the relationship between the crude oil emulsion viscosity and the water cut with the water cut (water content percentage) of the system as the x-axis and the crude oil emulsion viscosity as the y-axis; the water content percentage corresponding to the maximum viscosity of the crude oil emulsion is its phase inversion point.

Step 3: Measure the flow rate ratio of crude oil emulsion to crude oil when the water cut is less than or equal to the phase inversion point at the reservoir temperature, and then determine whether the flow rate ratio of crude oil emulsion to crude oil is within the range of 0.2 to 0.9; if it does, it indicates that water injection is applicable to the development of heavy oil reservoir.

The method for determining the flow rate ratio of crude oil emulsion to crude oil is as follows:

(1) Select natural or artificial cores (φ 3.8 cm×8 cm in size) that can represent the porosity and permeability of the reservoir, and vacuum the cores and saturate them with water;

(2) Inject crude oil into the core at a flow rate v corresponding to a shear rate of 150 s$^{-1}$ until the pressure is stable and record the stable pressure value $P_{crude\ oil}$; then inject the crude oil and produced water with a specific oil-water flow rate ratio at the same flow rate v into the core to simulate the formation of in-situ crude oil emulsion at a specific water cut, continue to inject until the pressure is stable, and record the stable pressure value $P_{emulsion}$; calculate the ratio of $P_{crude\ oil}$ to $P_{emulsion}$, which is the flow rate ratio of crude oil emulsion to crude oil at this water cut.

Wherein, the flow rate v is calculated as follows:

$$v = \frac{4n}{3n+1} \frac{\gamma\sqrt{150K\phi}}{12},$$

where, n is the flow behavior index, K is the permeability, in D, φ is the porosity, and γ is the shear rate.

(3) Repeat Step (1), then change the oil-water flow rate ratio, and repeat Step (2) to obtain the flow rate ratios of crude oil emulsion to crude oil at different water cuts.

The method for enhancing the recovery factor of heavy oil by in-situ oil-water emulsion with high phase inversion point disclosed in the present invention is technically characterized by water injection for developing heavy oil reservoir where the performance parameters of crude oil emulsion meet specific requirements, but its main oil displacement mechanism is completely different from conventional water flooding. In the process of oil displacement by in-situ emulsion with high phase inversion point, the crude oil emulsion can not only produce superimposed Jamin effect and increase the flow resistance in high water-cut areas, but more importantly, it can keep the oil as the external phase and the viscosity is several times that of crude oil, achieving both excellent fluidity and flow control effect. Meanwhile, influenced by the emulsion phase, the viscosity of the crude oil emulsion in the high-permeability zone (high water saturation) is always greater than that in the low-permeability zone (low water saturation), so its flow control effect is self-adaptive, effectively inhibiting the viscous fingering and stabilizing the front edge of oil-water displacement. In addition, a near-miscible "piston" displacement can be achieved between crude oil emulsion with oil as the external phase and heavy oil, which can improve wettability and produce a slippage effect on the rock wall, with the potential to greatly enhance the recovery factor of heavy oil by water flooding.

Compared with the prior art, the present invention has the following beneficial effects:

The method disclosed in the present invention is based on water flooding for heavy oil but different from conventional heavy-oil water flooding technology. It is a revolutionary application of crude oil-water thickening and emulsification, which can drive the water injected into heavy oil to reservoirs with crude oil viscosity as high as 6,000 m·Pas and significantly widen the upper viscosity limit of heavy-oil water injection, with broad application prospects and high economic benefits. The in-situ oil-water emulsion with high phase inversion point for oil displacement can adaptively control the flow rate and be nearly miscible with crude oil, while improving the wettability and the slippage effect on the rock wall, with the potential to greatly enhance the recovery factor of heavy oil by water flooding. The innovative application of viscous emulsification of heavy oil and water can intelligently enhance the recovery factor of heavy oil. In the present invention, the simple and easily available parameters are employed to identify the feasibility of in-situ emulsion with high phase inversion point in specific heavy oil reservoirs, which can contribute to the rapid production and application of the method in heavy oil production and provide key technical support for the quality improvement, efficiency enhancement and green development of heavy oil reservoirs.

Other advantages, objectives and characteristics of the present invention will be partly embodied by the following description, and partly understood by those skilled in the art through research and practice of the present invention.

DETAILED DESCRIPTION OF THE EMBODIMENTS

In the following detailed description of the preferred embodiments of the present invention, reference is made to the accompanying drawings. It is to be understood that the preferred embodiments described herein are only used to illustrate and interpret the present invention and are not intended to limit the present invention.

The heavy oil reservoir in Block J of Xinjiang Oilfield was studied as an example to explain the specific application of the method for enhancing the recovery factor of heavy oil by in-situ oil-water emulsion with high phase inversion point disclosed in the present invention.

Step 1: Measure the viscosity of the dehydrated heavy oil produced in Block J of Xinjiang Oilfield as 990 m·Pas at a reservoir temperature of 55° C., meeting the requirement of less than 6,000 m·Pas.

Figure 1:
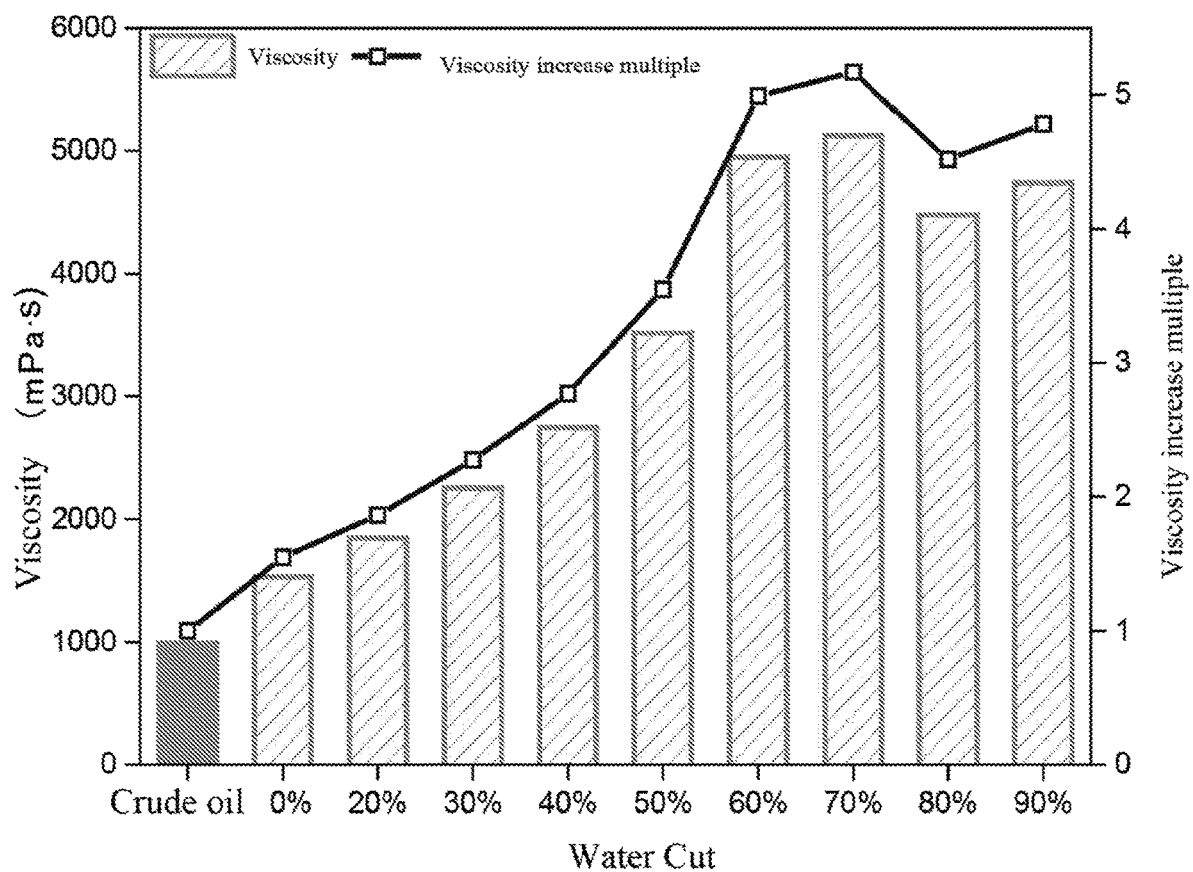
FIG. 1 is a bar chart of the viscosity and its increase multiple of crude oil emulsion formed at different water cuts (55° C.).

Step 2: Determine the viscosity and phase inversion point of the crude oil emulsion:

Preheat the dehydrated heavy oil and produced water to 55° C. respectively, and then mix the heavy oil and water at different volume ratios to control the water cuts as 10%, 20%, 30%, 40%, 50%, 60%, 70%, 80%, and 90%, respectively, with water cut=water volume/(total volume of crude oil and water), and use an emulsifier to stir the mixture under the condition of 55° C. and 150 s$^{-1}$ for 60 minutes to prepare crude oil emulsion; measure the apparent viscosity of the crude oil emulsion prepared at different water cuts under the condition of 55° C. and 7.34 s$^{-1}$ with a rotary viscometer, and develop a data analysis chart as shown in FIG. 1. The results show that the phase inversion point of the crude oil emulsion was 70%, and the emulsion viscosity corresponding to the phase inversion point was 5.17 times of the crude oil viscosity, meeting the requirement that the phase inversion point of the crude oil emulsion is greater than or equal to 70% and the emulsion viscosity corresponding to the phase inversion point is 2-6 times of the crude oil viscosity.

Step 3: Determine the flow rate ratio of crude oil emulsion to crude oil:

Select natural cores (φ3.8 cm×8 cm in size) from Block J of Xinjiang Oilfield, and vacuum the cores and saturate them with water; inject the dehydrated crude oil (with phase inversion point of 70%) into the core at a flow rate v corresponding to a shear rate of 150 s$^{-1}$ until the pressure is stable and record the stable pressure value $P_{crude\ oil}$; then inject the crude oil and produced water with different flow ratios (oil-water flow ratio: 4:1, 3:2, and 2:3) into the core at the same flow rate v until the pressure is stable, and record the stable pressure value $P_{emulsion}$; calculate the ratio of $P_{crude\ oil}$ to $P_{emulsion}$ to obtain the flow rate ratio of crude oil emulsion to crude oil at different water cuts. The experimental results are shown in Table 1, indicating that when the water cut was from 20% to 60%, the flow rate ratio of crude oil emulsion to crude oil was between 0.57 and 0.72, meeting the requirement that the flow rate ratio of crude oil emulsion to crude oil is 0.2 to 0.9.

TABLE 1

Flow Rate Ratios of Crude Oil Emulsion to Crude Oil at Different Water Cuts

| Core No. | Porosity (%) | Fluid-based permeability (md) | Oil-water flow ratio | Water cut (%) | Flow rate ratio |
|---|---|---|---|---|---|
| 50-2 | 15.6 | 32.8 | 4:1 | 20 | 0.57 |
| 50-8 | 17.4 | 24.3 | 3:2 | 40 | 0.72 |
| 50-10 | 15.5 | 28.7 | 2:3 | 60 | 0.59 |

Through the above Steps 1 to 3, it is judged that water injection is applicable to the development of the oil reservoir in Block J of Xinjiang Oilfield.

Figure 2:
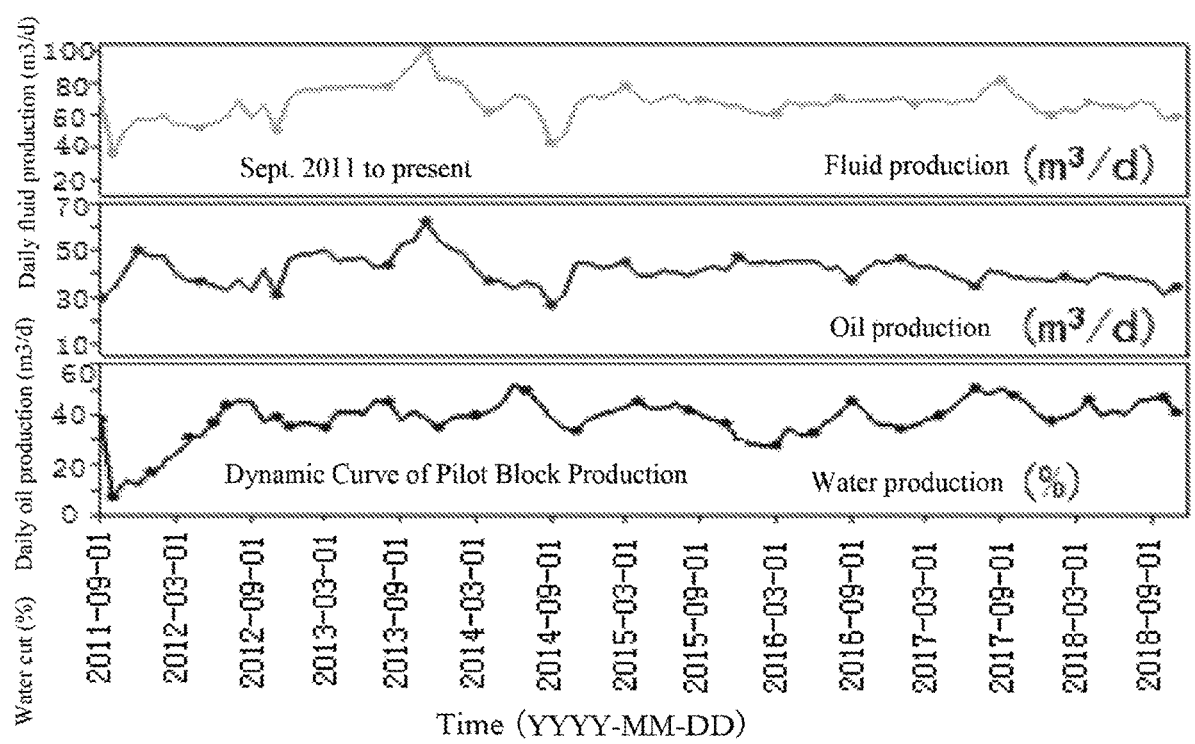
FIG. 2 is a dynamic curve of reservoir development in Block J of Xinjiang Oilfield.

The effect of field application of in-situ emulsification with high phase inversion point to heavy oil production is as follows: the viscosity of the crude oil in Block J of Xinjiang Oilfield was 900 to 2,000 m·Pas, the permeability was 100 mD, and the temperature was 55° C. According to the mechanism of conventional water flooding, it can be predicted that the recovery factor of this reservoir will be only 15% when the water cut reaches 98% by water flooding in this reservoir. However, due to the in-situ emulsification with high phase inversion point formed in the water injection for crude oil production (the phase inversion point of the crude oil emulsification is 70%), the water cut is only 40% (FIG. 2) and the recovery percent is higher than 18% after the water flooding has been applied to reservoir development for nearly 10 years. Thus, it can be seen that the method disclosed by the present invention is highly reliable.

The above are not intended to limit the present invention in any form. Although the present invention has been disclosed as above with embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. A method for enhancing a recovery factor of heavy oil by in-situ oil-water emulsion with high phase inversion point to develop a heavy oil reservoir comprising:
    performing water injection into a heavy oil reservoir under a condition when performance parameters of a crude oil emulsion meet three specific requirements, wherein the three specific requirements comprise:
    (A) viscosity of the crude oil is less than 6,000 mPa·s;
    (B) phase inversion point of the crude oil emulsion at reservoir temperature, is greater than or equal to 70%, and emulsion viscosity corresponding to the phase inversion point is two-to-six times of the crude oil viscosity; and
    (C) at the reservoir temperature, when water content is less than or equal to the phase inversion point, a flow rate ratio of crude oil emulsion to crude oil is 0.2 to 0.9.

2. The method for enhancing a recovery factor of heavy oil by in-situ oil-water emulsion with high phase inversion point according to claim 1, wherein the condition of performance parameters of crude oil emulsion meeting the three specific requirements is determined using the following steps:
    Step 1: taking a crude oil sample from the heavy oil reservoir, determining the crude oil viscosity, and determining whether the crude oil viscosity meets the requirement of less than 6,000 mPa·s; if it does, proceed to Step 2;
    Step 2: measuring the phase inversion point of the crude oil emulsion at the reservoir temperature, and determining whether the phase inversion point is greater than or equal to 70% and whether the emulsion viscosity corresponding to the phase inversion point is two-to-six times of the crude oil viscosity; if it does, proceed to Step 3;
    Step 3: measuring the flow rate ratio of crude oil emulsion to crude oil when the water content is less than or equal to the phase inversion point at the reservoir temperature, and then determining whether the flow rate ratio of crude oil emulsion to crude oil is within a range of 0.2 to 0.9, which indicates that water injection is applicable to the development of the heavy oil reservoir.

3. The method for enhancing a recovery factor of heavy oil by in-situ oil-water emulsion with high phase inversion point according to claim 2, wherein at the reservoir temperature in Step 2, the phase inversion point of the crude oil emulsion is determined using the steps of:
    Step (1) preheating the crude oil and produced water of the heavy oil reservoir to the reservoir temperature respectively;
    Step (2) mixing the preheated crude oil and produced water in different volume ratios to form a system with different measures of water content, and stirring the system with an emulsifier for 60 minutes at the reservoir temperature and shear rate of 150 s$^{-1}$ to form a crude oil emulsion;
    Step (3) measuring the viscosity of the crude oil emulsion at 7.34 s$^{-1}$ and reservoir temperature with a rotary viscometer; forming a curve based on a relationship between the crude oil emulsion viscosity and the different measures of water content, wherein the water content of the system is plotted on an x-axis and the crude oil emulsion viscosity on a y-axis; and determining a water content percentage corresponding to a maximum viscosity of the crude oil emulsion as the phase inversion point.

4. The method for enhancing a recovery factor of heavy oil by in-situ oil-water emulsion with high phase inversion point according to claim 2, wherein at the reservoir temperature in Step 3, the method for determining the flow rate ratio of crude oil emulsion to crude oil is as follows:

(1) Select natural or artificial cores that represent porosity and permeability of the reservoir, and vacuum the cores and saturate them with water;

(2) Inject crude oil into the cores at a flow rate v corresponding to a shear rate of 150 s$^{-1}$ until a pressure is stable and record a stable pressure value $P_{crude\ oil}$, then co-inject the crude oil and water produced in the cores with a specific oil-water flow rate ratio at the same flow rate v into the cores to simulate formation of in-situ crude oil emulsion at a specific water content, continue to inject until the pressure is stable, and record a stable pressure value $P_{emulsion}$; calculate a ratio of $P_{crude\ oil}$ to $P_{emulsion}$, which is the flow rate ratio of crude oil emulsion to crude oil at the specific water content;

(3) Repeat Step (1), then change the oil-water flow rate ratio, and repeat Step (2) to obtain the flow rate ratios of crude oil emulsion to crude oil at different measures of water content.

5. The method for enhancing a recovery factor of heavy oil by in-situ oil-water emulsion with high phase inversion point according to claim 4, wherein the flow rate v is calculated as follows:

$$v = \frac{4n}{3n+1} \frac{\gamma\sqrt{150K\phi}}{12},$$

where, n is a flow behavior index, K is permeability, in D, $\phi$ is porosity, and $\gamma$ is shear rate.

6. The method for enhancing a recovery factor of heavy oil by in-situ oil-water emulsion with high phase inversion point according to claim 4, wherein the natural or artificial cores are 3.8 cm×8 cm in size.

* * * * *